(12) United States Patent
Datta et al.

(10) Patent No.: US 6,423,092 B2
(45) Date of Patent: *Jul. 23, 2002

(54) BIODEGRADABLE STENT

(75) Inventors: Arindam Datta, Hillsborough; Shawn Thayer Huxel, Lakehurst; Dennis D. Jamiolkowski, Long Valley; Yufu Li, Bridgewater, all of NJ (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/933,096

(22) Filed: Aug. 20, 2001

Related U.S. Application Data

(62) Division of application No. 09/470,619, filed on Dec. 22, 1999.

(51) Int. Cl.[7] .................................................. A61F 2/06
(52) U.S. Cl. ...................................................... 623/1.15
(58) Field of Search ............................... 623/1.11–1.22, 623/1.38, 1.39, 1.4, 1.41–1.48, 1.49, 1.5, 1.51–1.53

(56) References Cited

U.S. PATENT DOCUMENTS

| | | | |
|---|---|---|---|
| 4,741,337 A | | 5/1988 | Smith et al. |
| 4,889,119 A | | 12/1989 | Jamiolkowski et al. |
| 5,059,211 A | * | 10/1991 | Stack et al. ................. 623/1.15 |
| 5,160,341 A | * | 11/1992 | Brenneman et al. ......... 606/198 |
| 5,185,408 A | * | 2/1993 | Tang et al. .................. 525/415 |
| 5,346,501 A | | 9/1994 | Regula et al. |
| 5,443,458 A | * | 8/1995 | Eury ............................ 623/13 |
| 5,626,611 A | | 5/1997 | Liu et al. |
| 5,629,077 A | * | 5/1997 | Turnlund et al. ........... 623/1.15 |
| 5,728,135 A | | 3/1998 | Bregen et al. |
| 5,766,710 A | * | 6/1998 | Turnlund et al. ........... 623/1.15 |
| 5,792,400 A | | 8/1998 | Talja et al. |
| 5,824,049 A | * | 10/1998 | Ragheb et al. .............. 623/1.15 |
| 5,873,904 A | * | 2/1999 | Ragheb et al. .............. 623/1.15 |
| 6,001,117 A | * | 12/1999 | Huxel et al. ................. 606/191 |
| 6,096,070 A | * | 8/2000 | Ragheb et al. .............. 623/1.15 |
| 6,117,168 A | * | 9/2000 | Yang et al. .................. 623/1.14 |
| 6,120,847 A | * | 9/2000 | Yang et al. .................. 623/1.14 |
| 6,153,252 A | * | 11/2000 | Hossainy et al. ........... 623/1.15 |
| 6,156,373 A | * | 12/2000 | Zhong et al. ............... 427/2.28 |
| 6,258,121 B1 | * | 7/2001 | Yang et al. ................. 623/1.46 |

FOREIGN PATENT DOCUMENTS

| | | | |
|---|---|---|---|
| EP | 0 523 743 A1 | 1/1993 | ........... A61L/17/00 |
| EP | 0 634 152 A1 | 1/1995 | ............. A61F/2/06 |
| WO | WO 90/04982 | 5/1990 | ........... A61L/27/00 |

* cited by examiner

*Primary Examiner*—Michael J. Milano
*Assistant Examiner*—(Jackie) Tan-Uyen T. Ho
(74) *Attorney, Agent, or Firm*—Emil Richard Skula

(57) ABSTRACT

A biodegradable stent for implantation into a lumen in a human body. The stent in one embodiment is made from a biodegradable fiber having an inner core and an outer layer. The outer layer is a blend of two polymer components. The inner core has a first degradation rate, and the outer layer has a second degradation rate. The second degradation rate is slower than the first degradation rate. The fiber softens in vivo such that the stent is readily passed from the lumen as a softened fragment or filament after a predetermined period of time through normal flow of body fluids passing through the lumen.

2 Claims, 13 Drawing Sheets

BIODEGRADABLE STENT

This is a Divisional Application of U.S. patent application Ser. No. 09/470,619, filed on Dec. 22, 1999 issued as U.S. Pat. No. 6,338,739 on Jan. 15, 2002.

FIELD OF THE INVENTION

The field of art to which this invention relates is medical devices, in particular, stent devices made from biodegradable polymers.

BACKGROUND OF THE INVENTION

The use of stent medical devices, or other types of endoluminal mechanical support devices, to keep a duct, vessel or other body lumen open in the human body has developed into a primary therapy for lumen stenosis or obstruction. The use of stents in various surgical procedures has quickly become accepted as experience with stent devices accumulates, and the number of surgical procedures employing them increases as their advantages become more widely recognized. For example, it is known to use stents in body lumens in order to maintain open passageways such as the prostatic urethra, the esophagus, the biliary tract, intestines, and various coronary arteries and veins, as well as more remote cardiovascular vessels such as the femoral artery, etc. There are two types of stents that are presently utilized: permanent stents and temporary stents. A permanent stent is designed to be maintained in a body lumen for an indeterminate amount of time. Temporary stents are designed to be maintained in a body lumen for a limited period of time in order to maintain the patency of the body lumen, for example, after trauma to a lumen caused by a surgical procedure or an injury. Permanent stents are typically designed to provide long-term support for damaged or traumatized wall tissues of the lumen. There are numerous conventional applications for permanent stents including cardiovascular, urological, gastrointestinal, and gynecological applications.

It is known that permanent stents, over time, become encapsulated and covered with endothelium tissues, for example, in cardiovascular applications. Similarly, permanent stents are known to become covered by epithelium, for example, in urethral applications. Temporary stents, on the other hand are designed to maintain the passageway of a lumen open for a specific, limited period of time, and preferably do not become incorporated into the walls of the lumen by tissue ingrowth or encapsulation. Temporary stents may advantageously be eliminated from body lumens after a predetermined, clinically appropriate period of time, for example, after the traumatized tissues of the lumen have healed and a stent is no longer needed to maintain the patency of the lumen. For example, temporary stents can be used as substitutes for in-dwelling catheters for applications in the treatment of prostatic obstruction or other urethral stricture diseases. Another indication for temporary stents in a body lumen is after energy ablation, such as laser or thermal ablation, or irradiation of prostatic tissue, in order to control post-operative acute urinary retention or other body fluid retention.

It is known in the art to make both permanent and temporary stents from various conventional, biocompatible metals. However, there are several disadvantages that may be associated with the use of metal stents. For example, it is known that the metal stents may become encrusted, encapsulated, epithelialized or ingrown with body tissue. The stents are known to migrate on occasion from their initial insertion location. Such stents are known to cause irritation to the surrounding tissues in a lumen. Also, since metals are typically much harder and stiffer than the surrounding tissues in a lumen, this may result in an anatomical or physiological mismatch, thereby damaging tissue or eliciting unwanted biologic responses. Although permanent metal stents are designed to be implanted for an indefinite period of time, it is sometimes necessary to remove permanent metal stents. For example, if there is a biological response requiring surgical intervention, often the stent must be removed through a secondary procedure. If the metal stent is a temporary stent, it will also have to be removed after a clinically appropriate period of time. Regardless of whether the metal stent is categorized as permanent or temporary, if the stent has been encapsulated, epithelialized, etc., the surgical removal of the stent will resultingly cause undesirable pain and discomfort to the patient and possibly additional trauma to the lumen tissue. In addition to the pain and discomfort, the patient must be subjected to an additional time consuming and complicated surgical procedure with the attendant risks of surgery, in order to remove the metal stent.

Similar complications and problems, as in the case of metal stents, may well result when using permanent stents made from non-absorbable biocompatible polymer or polymer-composites although these materials may offer certain benefits such as reduction in stiffness.

It is known to use bioabsorbable and biodegradable materials for manufacturing temporary stents. The conventional bioabsorbable or bioresorbable materials from which such stents are made are selected to absorb or degrade over time, thereby eliminating the need for subsequent surgical procedures to remove the stent from the body lumen. In addition to the advantages attendant with not having to surgically remove such stents, it is known that bioabsorbable and biodegradable materials tend to have excellent biocompatibility characteristics, especially in comparison to most conventionally used biocompatible metals. Another advantage of stents made from bioabsorbable and biodegradable materials is that the mechanical properties can be designed to substantially eliminate or reduce the stiffness and hardness that is often associated with metal stents, which can contribute to the propensity of a stent to damage a vessel or lumen.

However, there are disadvantages known to be associated with the use of bioabsorbable or biodegradable stents. The disadvantages arise from the limitation of the material from which the stent is made. One of the problems associated with the current stents is that the materials break down too quickly. This improper breakdown or degradation of a stent into large, rigid fragments in the interior of a lumen, such as the urethra, may cause obstruction to normal flow, such as voiding, thereby interfering with the primary purpose of the stent in providing lumen patency. Alternatively, they take a long time to breakdown and stay in the target lumen for a considerable period of time after their therapeutic use has been accomplished. There is thus a long-term risk associated with these materials to form stones when implanted in a urine environment, for example, the urethra.

Accordingly, there is a need in this art for novel, temporary stents made from biodegradable polymers, wherein the stents remain functional in a body lumen for the duration of a prescribed, clinically appropriate period of time to accomplish the predetermined therapeutic purpose, and, then degrade without breaking down into large, rigid fragments, which may cause irritation, obstruction, pain or discomfort to the patient.

In a preferred embodiment of the present invention, the temporary stent readily passes out of the body as very soft particles or soft fibrous element or elements, and irritation, obstruction, pain or discomfort to the patient is either eliminated, or if present, is minimal.

SUMMARY OF THE INVENTION

It is an object of the present invention to provide a stent for insertion into a body lumen which is manufactured from biodegradable polymers, and which is easily passed from the body lumen after a specific therapeutic period of time.

It is a further object of the present invention to provide a biodegradable polymeric composition that can be used to make such temporary stents, and that would degrade, breakdown and pass out of the body lumen causing little or no irritation, obstruction, pain and discomfort without being substantially absorbed in the body.

It is yet a further object of the present invention to provide a stent made from a member having an inner core having a first in vivo degradation rate and an outer layer having a second in vivo degradation rate.

Therefore, an implantable stent is disclosed for use in body lumens, wherein such lumens exist as part of the natural anatomy or are made surgically. The stent is an elongate, hollow member such as a tubular structure or a helical structure, and in a preferred embodiment has a helical structure having a plurality of coils made from a wound fiber. The stent has a longitudinal axis and a longitudinal passage. The coils have a pitch. The helical stent is made from a filament or a fiber having an inner core. The inner core has an exterior surface. Optionally, the inner core is hollow. The filament or fiber also has an outer layer, coating or structure covering the exterior surface of the inner core. The filament or fiber has a cross-section. The rates of degradation of the inner core and outer layer are selected such that the rate of degradation of the inner core is faster than the degradation rate of the outer layer. This effectively provides that the inner core degrades in vivo, and loses it's mechanical integrity and is substantially eliminated from the lumen prior to the degradation of the outer layer, while the outer layer remains in place. The inner core is made from a biodegradable polymer made from the monomers selected from the group consisting of lactide, glycolide, paradioxanone, caprolactone, and trimethylene carbonate, caprolactone, blends thereof and copolymers thereof. Again, an important characteristic of the material with is used to make the inner core is that it has a first degradation rate and that this degradation rate is higher or faster than the degradation rate of the outer layer having a second degradation rate.

The outer layer or outer structure comprises a blend of at least two polymers or co-polymers. The blend will contain at least one faster degrading polymer and one slower degrading polymer. More specifically, the outer layer or outer shell, comprises a blend of at least two polymers, the first of said polymers being a glycolide-rich, lactide/glycolide copolymer containing at least 80 mole percent of polymerized glycolide, the other of said polymers being a lactide-rich copolymer containing at least 50 mole percent of polymerized lactide. The overall blend contains at least 50 weight percent of the glycolide-rich copolymer and at least 5 weight percent of lactide-rich copolymer with, preferably, the overall blend containing about 38 to about 97 weight percent of polymerized glycolide.

Preferably, the outer layer or outer shell comprises a blend of at least two polymers, the first of said polymers being, a glycolide-rich, lactide/glycolide copolymer containing at least 80 mole percent of polymerized glycolide, and another of said polymers being a lactide-rich, lactide/glycolide copolymer, containing at least 50 mole percent of polymerized lactide. The polymeric components of the overall blend (that is, not counting non-polymeric components such as barium sulfate) will contain at least 50 weight percent of the glycolide-rich copolymer and at least 20 weight percent of lactide-rich copolymer with the overall blend containing about 38 to about 89 weight percent of polymerized glycolide and the rest being polymerized lactide.

Most preferably, the outer layer or outer shell, comprises a blend of at least two polymers, the first of said polymers being the glycolide-rich copolymer, 10/90 lactide/glycolide copolymer, the second of said polymers being the lactide-rich copolymer, 85/15 lactide/glycolide copolymer. The polymeric components of the overall blend (that is, not counting non-polymeric components such as barium sulfate) will contain about 60 weight percent of the glycolide-rich copolymer (10/90 lactide/glycolide copolymer) and about 40 weight percent of the lactide-rich copolymer (85/15 lactide/glycolide copolymer), with the overall blend containing about 60 weight percent of polymerized glycolide and about 40 polymerized lactide.

The inner core typically degrades by hydrolysis and breaks down at a faster rate than the outer layer with exposure to body fluids. The inner core breaks down into small granular particles that are removed easily by the body fluids. The outer layer degrades or erodes into a fibrillar morphological structure. The faster degrading core, after sufficient in vivo exposure, possesses little or no mechanical integrity and is slowly removed, reducing the stent cross-section from a solid to a soft structure that increasingly appears to be hollow. With hydrolytic exposure, the progressively degrading stent can readily pass out of the body lumen, thereby minimizing the possibility of causing obstruction, pain or discomfort. Both the inner core and outer shell although degradable, do not bio-absorb and their degradation products are passed through and out of the body lumen. In one embodiment of the present invention, the device is rendered soft and pliable in vivo, thereby allowing it to easily pass out of the lumen in substantially a unitary piece. In another embodiment, the device not only is rendered soft and pliable, it breaks down into smaller discrete non-occluding pieces that pass out of the lumen.

Yet another aspect of the present invention is the above-described stent made from a fiber that is radio-opaque.

Still yet another aspect of the present invention is the above-described stent having only the outer layer without the inner core.

Another aspect of the present invention is the above-described fiber used to make a stent having a helical structure.

Yet another aspect of the present invention is a method of using the stents of the present invention in a surgical procedure to maintain the patency of a body lumen. A stent of the present invention is provided. The stent is an elongate, hollow member and in a preferred embodiment has a helical structure having a plurality of coils. The member has a longitudinal axis. The coils have a pitch. The structure is made from a filament or a fiber having an inner core. The inner core has an exterior surface. Optionally, the inner core is hollow. The filament or fiber also has an outer layer covering substantially all of the exterior surface of the inner core. The filament or fiber has a cross-section. The rates of degradation of the inner core and outer layer are selected to effectively provide in a preferred embodiment such that the rate of degradation of the inner core is higher than the degradation rate of the outer layer to effectively provide that the inner core degrades in vivo, and loses it's mechanical integrity and is substantially removed from the lumen prior to elimination of the degradation of the outer layer. The inner core typically degrades by hydrolysis and breaks down at a faster rate than the outer layer with exposure to body fluids; the outer layer degrades or erodes into a soft, fibrous morphology. The stent is inserted into the body lumen of a patient, thereby providing for the patency of the lumen for a specific range of times. The stent is maintained in the lumen for a sufficient period of time to effectively maintain the lumen open and to effectively let the inner core degrade such that the softened outer core may be passed through the lumen.

Still yet another aspect of the present invention are the above-described stents and fibers, wherein the slower degrading polymeric blend is used for the core, and the faster degrading polymeric material is used as the outer layer or structure.

These and other aspects of the present invention will become more apparent from the following description and examples, and accompanying drawings.

DESCRIPTION OF THE PREFERRED EMBODIMENTS

Figure 1:
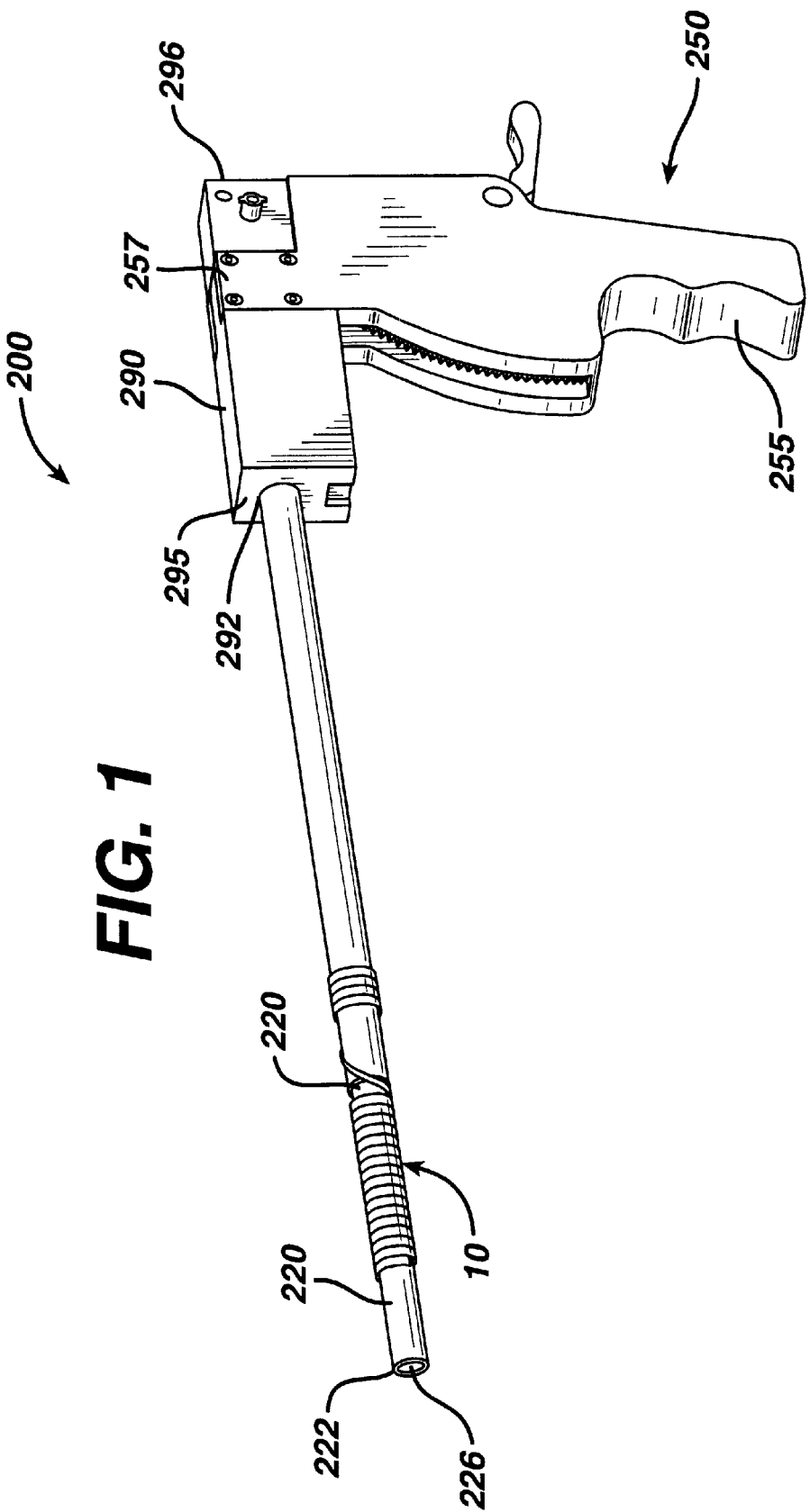
FIG. 1 is a perspective view of a preferred embodiment of a stent device of the present invention mounted to the distal end of an applicator instrument.
Figure 2:
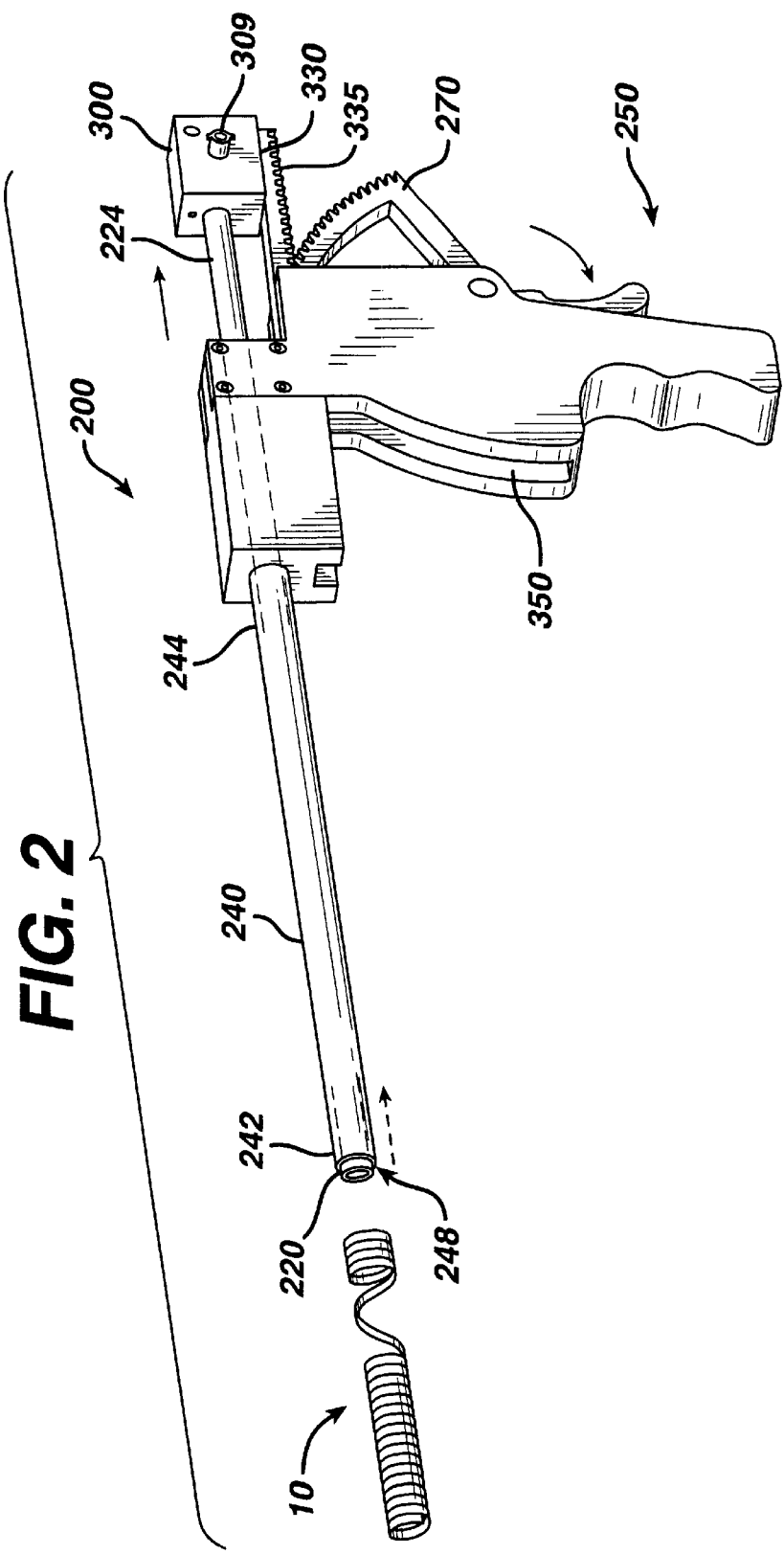
FIG. 2 is a perspective view of the stent and applicator of FIG. 1, prior to loading the stent onto the applicator instrument.
Figure 3:
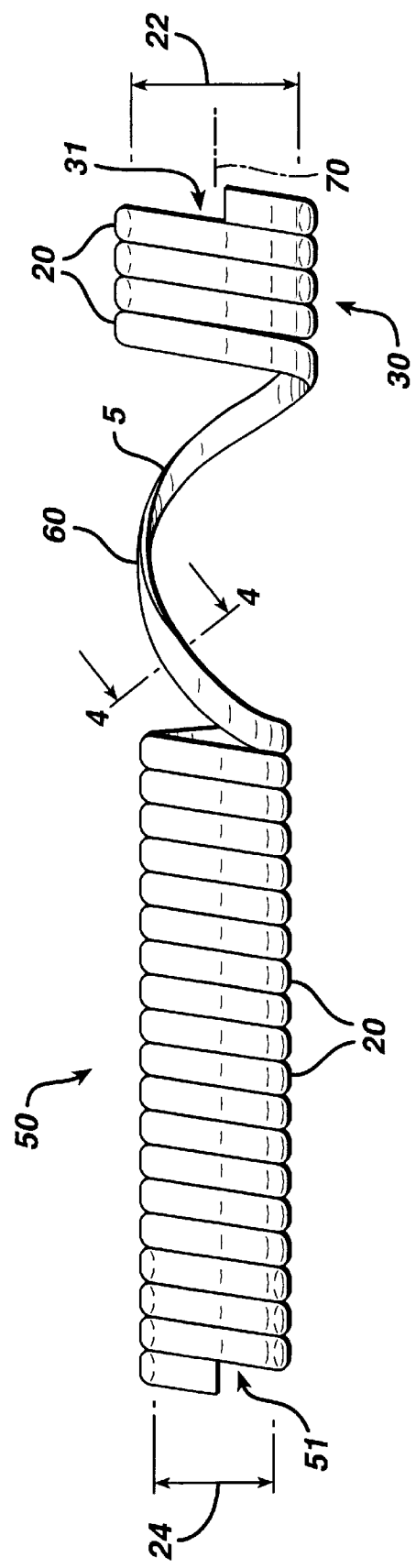
FIG. 3 is a side view of a stent device of the present invention, having a helical configuration.
Figure 4:
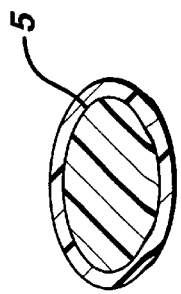
FIG. 4 is a cross-sectional view of the fiber used to make the stent of FIG. 3 taken along View Line 4—4 illustrating an oval cross section.
Figure 5:
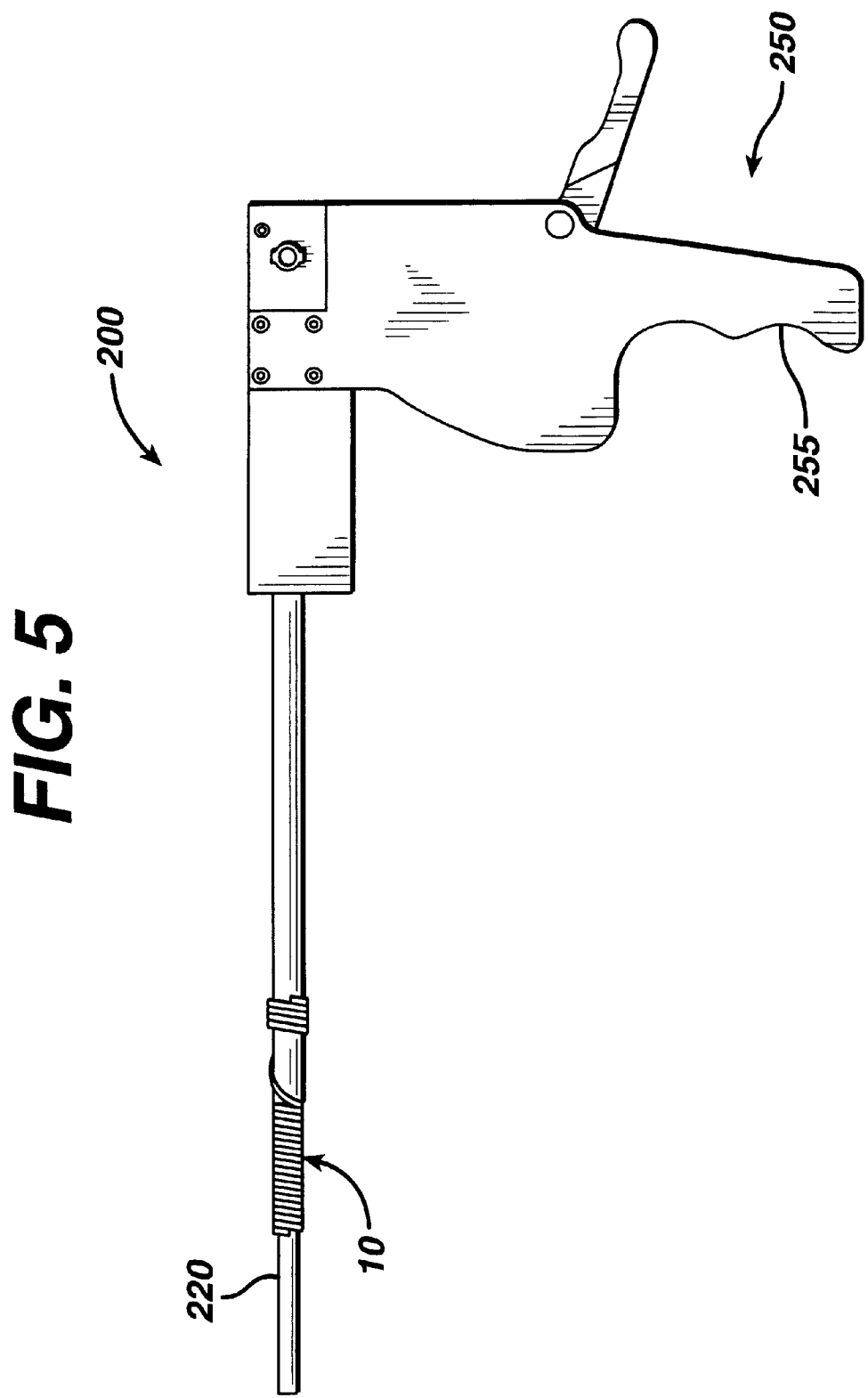
FIG. 5 is a side view of the stent and applicator device of FIG. 1, where the device is shown in the ready position, prior to application.
Figure 6:
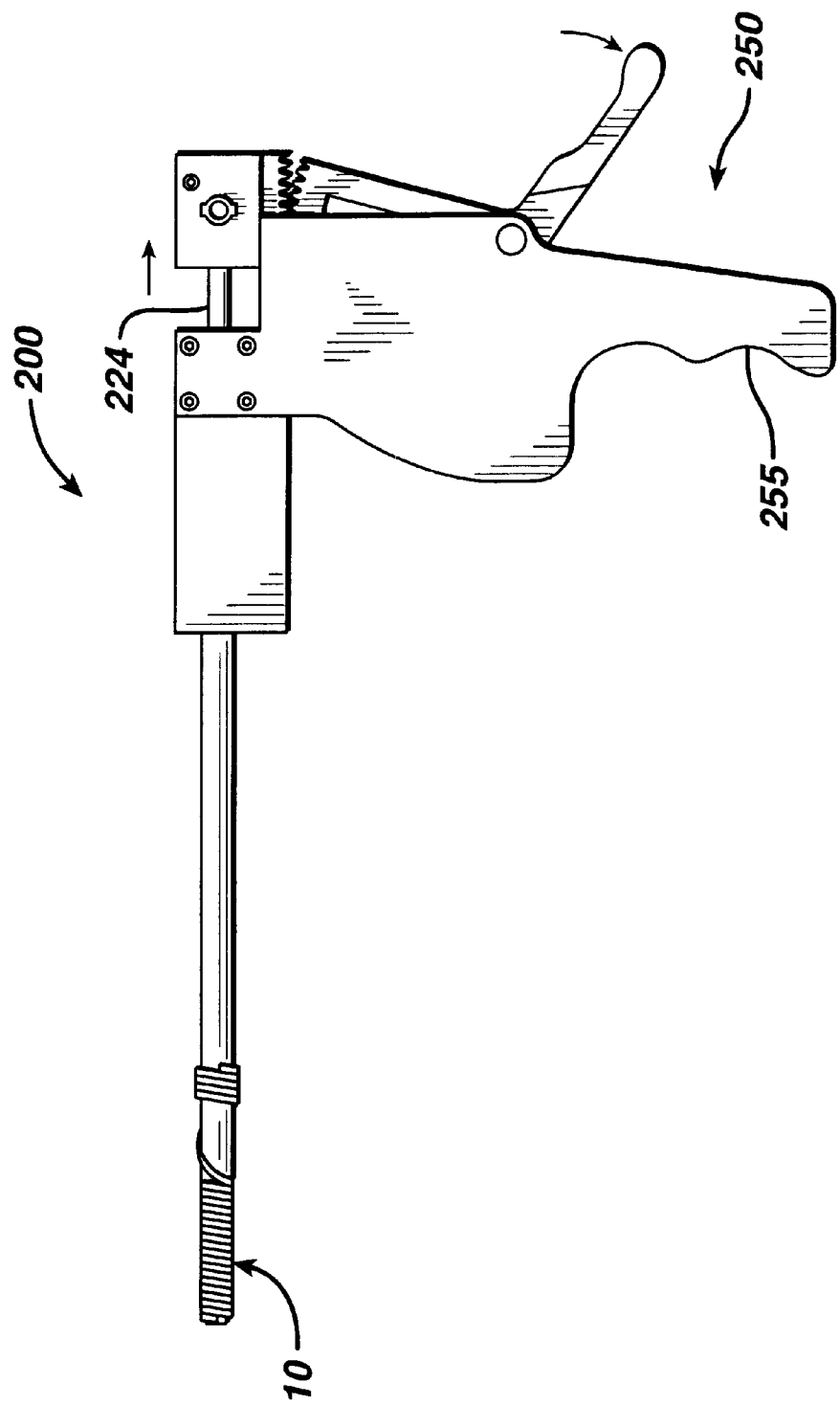
FIG. 6 is a side view of the stent and applicator device of FIG. 5, illustrating the position of the stent relative to the applicator when the stent is partially deployed by engaging the applicator trigger.
Figure 7:
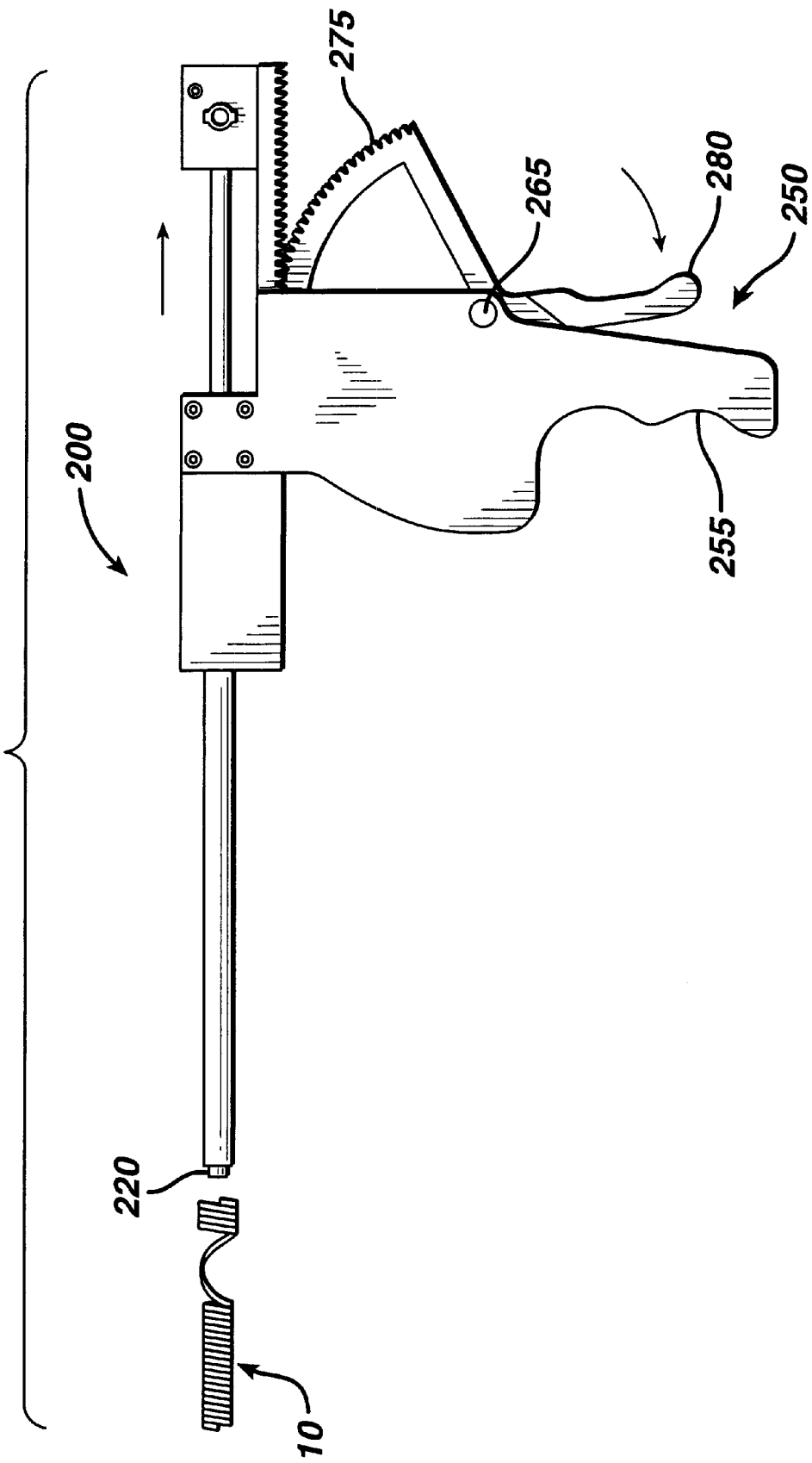
FIG. 7 illustrates the relative positions of the stent to the applicator of FIG. 6 when the stent is fully deployed by fully engaging the applicator trigger.
Figure 10:
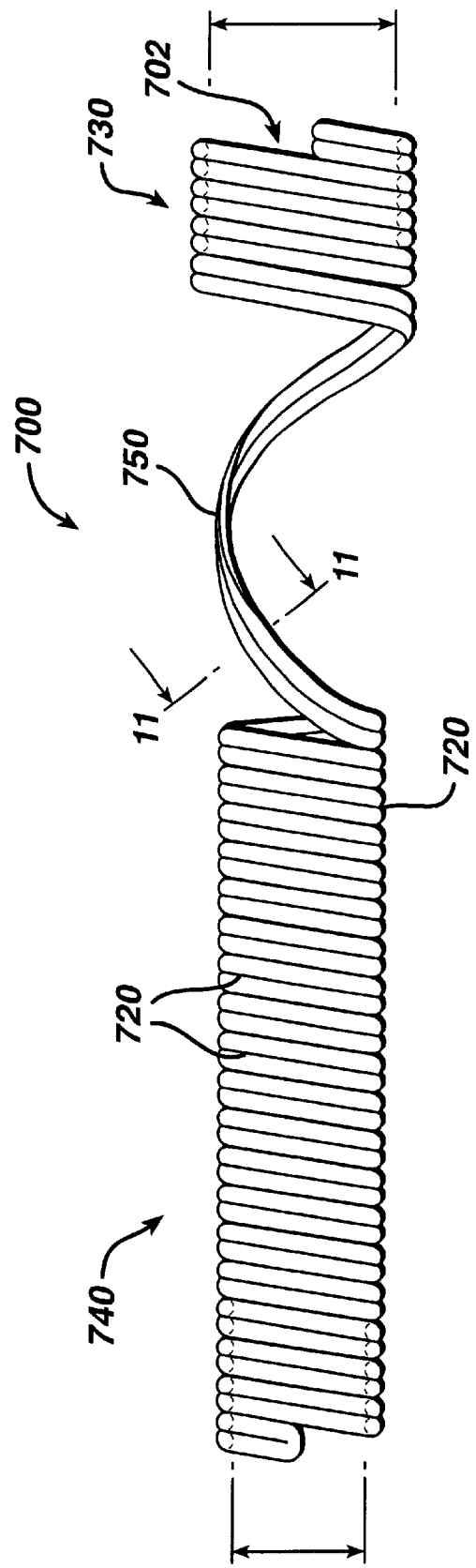
FIG. 10 illustrates an alternative embodiment of a stent of the present invention wherein a double fiber is used to make the stent.
Figure 11:
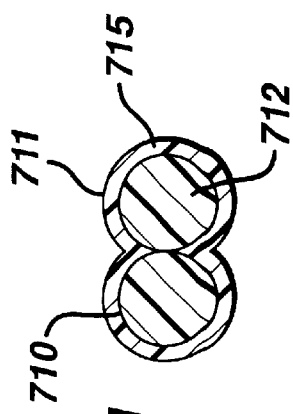
FIG. 11 is a cross-sectional view of the stent of FIG. 10 taken along View Line 11—11; the fibers are seen to have a circular cross-section.
Figure 15:
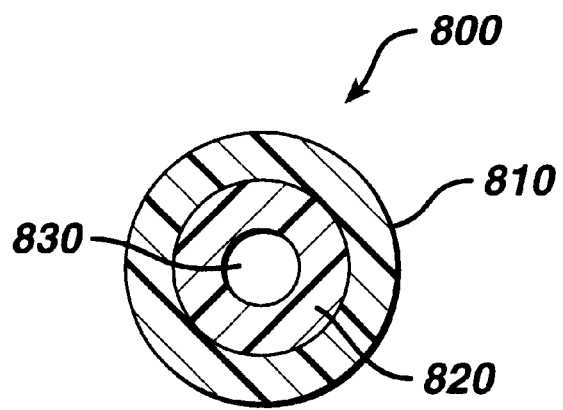
FIG. 15 is an end view of a fiber of the present invention having a hollow passageway through the inner core.

Referring to FIGS. 1–9, a preferred embodiment of a stent of the present invention is illustrated. As seen in FIG. 3, the stent 10 is seen to be a helical structure having a series of connected coils 20. The coils are made from fiber 100. The term fiber as used herein is defined to include not only fibers but filaments as well. It is preferred that fiber 100 be a continuous fiber, however, it is possible to make stent 10 from two or more sections of fiber which are subsequently connected or hinged together. As seen in FIG. 4, the fiber 100 is seen to have inner core 110 and outer layer or covering 130. The inner core 110 is seen to have outer surface 115. Covering the outer surface 115 of inner core 110 is the outer layer or section 130. outer layer 130 is seen to have inner surface 135 and exterior surface 140. Preferably, inner surface 135 is in contact with, and affixed to, the outer surface 115. The outer layer 130 is referred to herein as a structure, layer or coating. For example, it may be coated onto core 110, coextruded with core 110, or subsequently mounted or affixed onto core 110. The stent is seen to have a longitudinal axis 70, and internal passageway 11. The stent 10 is seen to have a first distal section 30 of coils 20 connected to a second section 50 of coils 20, wherein the sections 30 and 50 are connected by hinged connecting fiber 60. The distal section 30 of coils adjacent to hinged connecting fiber 60 forms an anchoring section which is inserted distal to the external sphincter. The proximal section 50 of the stent 10 is maintained within the prostatic urethra. Proximal section 50 is seen to have coils 20 having diameter 24, and also has passageway 51. The distal section 30 of stent 10 has coils 20 having a diameter 22. Distal section 30 also has a passageway 31. Passage ways 31 and 51 are in communication to form passageway 11 of stent 10. As seen in FIG. 4, one preferred embodiment of the stent 10 of the present invention has a fiber 100 having an oval cross-sectional configuration. The fiber 100 may have various configurations depending upon the application including round, square, polygonal, curved, oval, and combinations thereof and equivalents thereof. Those skilled in the art will appreciate that certain cross-sectional configurations will provide different advantages in the stent. For example, the advantages of fiber of the present invention having an oval cross-section include ease of the stent manufacturing process due to a possible on-line, one-step transition from the fiber to the stent in future manufacturing processes, flexibility during the stent deployment by being able to tailor the length of the stent during a surgical procedure to fit a particular patient's anatomy, and possible enhanced mechanical capabilities. Additionally, the core sections of the oval fibers are susceptible to faster degradation than the round fibers leading to a more palpable degradation product. A softer degradation product will be less irritable and cause less discomfort during ultimate passage. If desired, the fiber 100 may additionally have a hollow longitudinal passageway as illustrated in FIG. 15, wherein a fiber 800 has an outer layer 810, an inner core 820, and a hollow longitudinal passage 830 within core 820. Another embodiment of a helical stent of the present invention is illustrated in FIGS. 10–11. The stent 700 is seen to be made from double fibers 710 having inner cores 712 and outer cores 715. The stent is seen to have a plurality of coils 720, first section 730 and second section 740 joined by hinged connecting section 750. The stent 700 is seen to have longitudinal passage 702. The fibers 710 have a circular cross-section and are preferably connected together at several locations along the length of each fiber.

Figure 12:
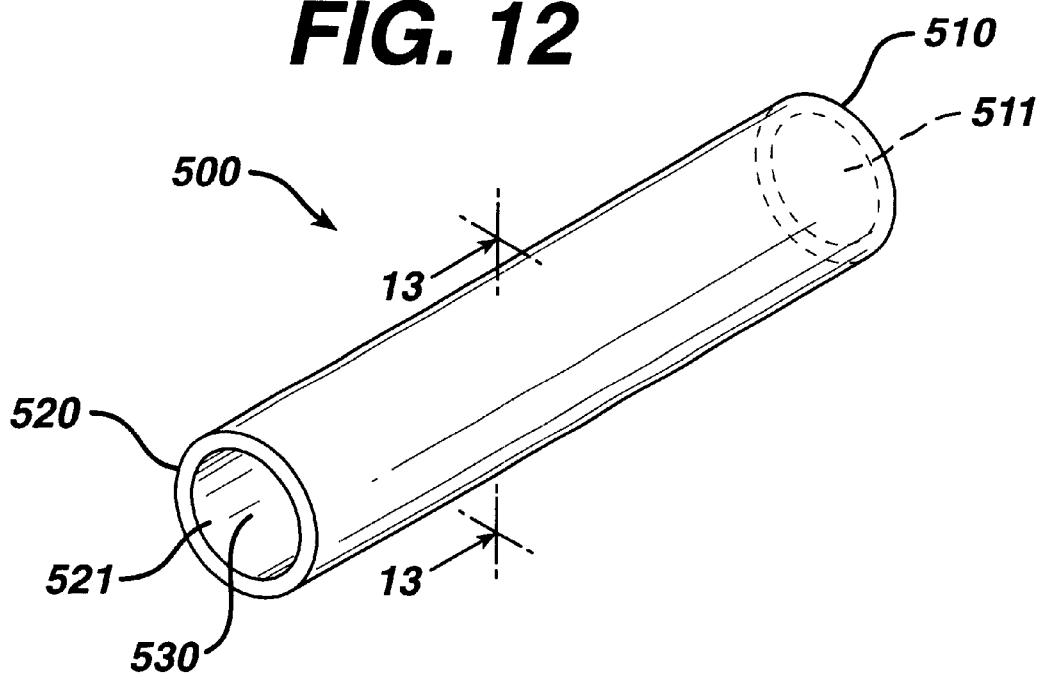
FIG. 12 is a perspective view of an alternate embodiment of a stent of the present invention, wherein the stent has a tubular configuration.
Figure 13:
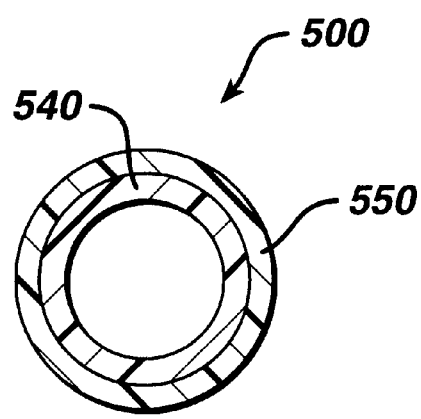
FIG. 13 is a cross-sectional view of the stent of FIG. 12 taken along View Line 13—13.
Figure 14:
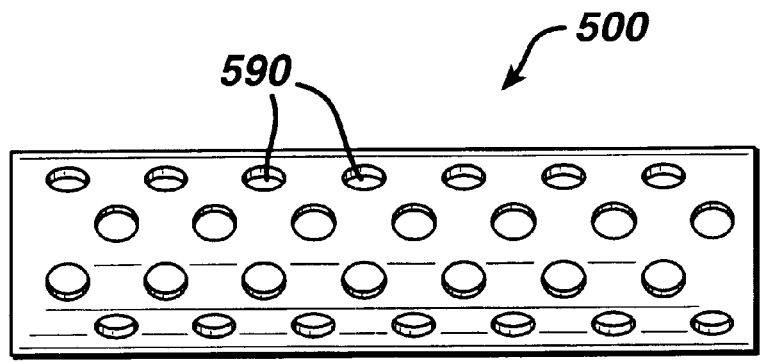
FIG. 14 is a perspective view of an alternate embodiment of a stent of the present invention having a tubular configuration with latticed openings.

Another embodiment of a stent of the present invention is seen in FIG. 12. The stent 500 is seen to have a tubular configuration having ends 510 and 520, as well as inner passageway 530 in communication with openings 511 and 521 in ends 510 and 520, respectively. The stent is seen to have inner core section 540 and outer layer or structure 550. If desired, the stent 500 may have a variety of conventionally shaped openings 590 extending through the outer structure 550 and inner core 530, arranged in a pattern such as a lattice, as seen in FIG. 14. If desired, the openings 590 can extend only through outer structure 550. A cross-sectional view of stent 500 is illustrated in FIG. 13, where the inner core section 540 and the outer layer or structure 550 can be readily seen.

Although not particularly preferred, the stents of the present invention can be manufactured from fibers without an inner core. That is, the fibers would only have the degradable outer layer without the inner core. Such fibers could be solid, or could have a hollow passageway. Similarly, if a tubular configuration were desired, it could be made with no inner core, while having a hollow passageway and would be made entirely from the polymeric composition used for the outer core.

The stent 10 is preferably manufactured from a bioabsorbable polymeric fiber 100 having a desired cross-sectional configuration. The length and overall diameter of the stent 10 will depend upon a number of factors including the anatomy of the patient, the size of the anatomy and the type of surgical procedure which has effected the urethral lumen. For example, the overall length of a stent 10 useful in the practice of the present invention will be sufficient to effectively maintain the lumen passage open. Typically the length for urethral applications in and adult male, the length will be about 10 mm to about 200 mm, more typically about 20 nm to about 100 mm, and preferably about 40 mm to about 80 mm. The diameter of a stent 10 of the present invention will be sufficient to effectively maintain patency of the lumen. For prostatic urethral applications, where the stent has two sections having different diameters, typically the diameter in the prostatic urethra will typically be about 2 mm to about 25 mm, more typically about 4 mm to about 15 mm, and preferably about 6 mm to about 10 mm. The diameter of the section used to anchor distal to the external sphincter will be about 2 mm to about 25 mm, more typically about 4 mm to about 15 mm, and preferably about 6 mm to about 10 mm. The major cross-sectional dimension of a fiber used to manufacture a stent of the present invention will be sufficient to provide effective support and flexibility. Typically, when utilizing a circular cross-section, the diameter for urethral applications will be about 0.1 mm to about 4 mm, more typically about 0.5 mm to about 3 mm, and preferably about 1 mm to about 2 mm. The pitch, length, diameter and fiber diameter of the stents of the present invention will be sufficient to effectively provide sufficient support in response to radial stress of the urethral vessel walls, while providing for ease of insertion and stability while inserted in the urethral lumen, as well as desired flexibility and lumen patency. The pitch of the stent is defined to be the number of coils per unit length. In this patent application specification, for this example, pitch is defined as the number of coils per centimeter of stent length. Typically, for urethral applications, the pitch will be about 2.5 to about 100, more typically about 3 to about 20, and preferably about 5 to about 10. Although it is preferred for urethral applications that there be no space between adjacent coils, the stents of the present invention may have spaces between adjacent coils.

It is also possible for the stents of the present invention to have in addition to wound fiber structures, such as tubular members, latticed members and the like. Examples of a tubular stent are illustrated in FIGS. 12–14. Those skilled in the art will appreciate that such structures could be made from woven cloth, mesh, flat stock that is rolled into shape, and the like. Such structures could have the inner core and outer layer, similar to the fibers and helical stents of the present invention, or may simply be made from the blend materials used to make the outer section.

In addition, it should be noted that an alternate embodiment of the stents and fibers of the present invention is to have the slower degrading polymer component as the inner core and the faster degrading polymer component as the outer section. The faster degrading outer core would sluff off or degrade over time leaving behind the softening inner core, which would then be expelled or removed from the lumen. The polymer components would be the same as for the other embodiments, that is, for the faster degrading and slower degrading components.

The fibers of the present invention will preferably be made to have an inner core consisting of a first biodegradable polymer composition and an outer core consisting of a second biodegradable polymer composition. The inner polymer core material will be selected such that the inner core will degrade by hydrolysis and lose mechanical integrity at a relatively faster rate than the outer shell upon exposure to body fluids over time. The inner core material breaks down preferably into small granular particles that are removed easily by the body fluids. A portion of the outer polymer coating will be selected to have a relatively slow rate of hydrolysis that would preferably degrade or erode and expose a fibrillar morphological structure after in vivo exposure to body fluids. The fibrillar morphology of the outer layer aids the dispersion of degradation products of the faster degrading inner core.

The fibrillar morphology of the outer layer is a consequence of the polymer blend composition and the process conditions used to produce it. The fibrillar morphology allows the outer layer to soften with time rather than break up into large pieces that can cause obstruction or occlusion in the lumen. In a different embodiment of the present invention, the fiber is of solid or hollow cross-section preferably with an inner core and an outer layer made from polymer blend.

The slower degrading shell is fibrillar and the faster degrading core posses no significant mechanical integrity and is slowly removed. The effect of the differing degradation profiles and the physical state of the degraded polymers reduce the stent cross-section from a solid to a soft structure that increasingly appears to be hollow. The fibrillar structure will soften over time instead of breaking down into large, sharp fragments that can cause the removal and/or passage of the degraded stent to be clinically eventful. In a flow environment, the progressively degrading stent can readily pass through the body lumen without causing obstruction, pain or discomfort. Both the inner core and outer shell do not bio-absorb into the lumen wall as their degradation products are passed from the body lumen.

A stent must be designed to withstand radial stresses in order to perform its function of maintaining a passage through a lumen open. The mechanical capability of the stents of the present invention to withstand radial stresses when the stent is emplaced in the body lumen is provided primarily by the biodegradable material in the outer shell layer. The strength, stiffness, and thickness of this material in the outer shell are sufficient to effectively withstand the loads necessary to keep the stent functional. As the inner core degrades and breaks down, the outer shell wall having a sufficient thickness of properly selected biodegradable material would effectively be able to withstand the load necessary for the time period required to keep the lumen patent. In essence then, the annular shell can be designed to fulfill the mechanical requirements of keeping the body lumen patent or open for the specific therapeutic time period. The inner core, in addition to being designed to degrade into small granular-like fragments, can also be filled with other conventional materials that can satisfy other functional needs such as a carrier of radio opaque markers or as potential processing aids during stent manufacturing. For example, a filled core can reduce the "flattening" of the fiber that is sometimes possible when a hollow stent is wound at high temperatures.

A proper selection of degradation rates will cause the inner core to fracture into small pieces in vivo, while a portion, or all, of the outer layer remains intact, thereby producing unique "soft" fragments or filaments. That is, after the inner core has degraded and effectively been removed from the stent structure by body fluids, the remaining outer layer degrades to a soft, pliable, fibrillar filament, which may remain intact or degrade into several sections. The remaining soft filament, or pieces thereof, is readily excreted from the lumen.

As mentioned previously, although not preferred, it is possible to manufacture the stents of the present invention from fibers having no inner core, but only the outer layer material. Such fibers could be hollow or solid. Similarly, tubular stents of the present invention could also be manufactured without the inner core. When manufacturing such embodiments, it would not be necessary to use co-extrusion. Otherwise, the requirements for the stents in terms of mechanical strength and degradation rates would be similar.

Polymer materials useful in the stents and fibers of the present invention include those biodegradable polymers disclosed in U.S. Pat. No. 4,889,119 which is incorporated by reference. In those embodiments of the subject invention utilizing an inner core, the inner core comprises a polymer or polymers having a biodegradation rate higher than that of the outer layer or outer shell. The polymers used to manufacture the inner core will include polymers sufficiently effective to hydrolyze, degrade and breakdown at a relatively faster rate compared to the material in the shell. Preferably, these polymers include those made utilizing the monomers of lactide, glycolide, para-dioxanone, trimethylene carbonate and caprolactone. When the term "caprolactone" is used herein it is meant to mean epsilon-caprolactone. These monomers can be used to make copolymers that can have random, block or segmented block sequences, or combinations thereof. Of particular utility are the segmented block copolymers of glycolide and caprolactone containing about 75 mole % of polymerized glycolide and about 25 mole % of polymerized caprolactone. Combinations of copolymers thereof can be employed.

The polymeric materials used for the outer layer of the stents of the present invention are selected from polymers sufficiently effective to hydrolyze, degrade and breakdown at a relatively slower rate and preferably form a fibrillar morphological structure upon in vivo exposure. Preferably, the polymers which can be utilized to form the outer layer include polylactide, polyglycolide, polyparadioxanone, and polycaprolactone and combinations thereof, copolymers thereof and equivalents thereof. It is particularly preferred to use a blend of at least two polymers or co-polymers in the outer shell. The blend will contain at least one faster degrading polymer and one slower degrading polymer. It is preferable, though not essential, that there is some compatibility between the two polymers in the outer shell but also that the two components are somewhat immiscible. For the outer shell, it is particularly preferred to use a blend of a glycolide copolymer containing at least 80 mole percent of polymerized glycolide, the other of the said polymer being polylactide copolymer containing at least 50 mole percent of polymerized lactide. The overall blend will contain at least 50 weight percent of the glycolide copolymer and at least 5 weight percent of lactide copolymer with the overall blend containing about 38 to about 97 weight percent of polymerized glycolide and the rest being polymerized lactide.

The fibers useful in manufacturing the stents of the present invention have an inner core of a first biodegradable material having a first degradation rate and an outer layer of a second biodegradable material having a second degradation rate can be manufactured using a variety of conventional techniques including conventional co-extrusion processing. For example, a fiber may be formed by feeding a first polymer composition to a first pump on a conventional co-extruder, and a second polymer composition to a second pump on a conventional co-extruder. The first pump directs the first polymer composition to the interior of a co-extrusion die, while the second pump directs the second polymer composition to the outer concentric section of the co-extrusion die, thereby forming a fiber having an inner core and an outer layer. If desired, the fibers of the present invention may be made by other conventional processes including melt coating, solution coating or powder coating followed by spreading the coating by melting, etc., and the like. For example, when using a coating process, the inner core can be a mono-filament extruded material or can be made from a multi-filament braid. The outer shell layer can be added on top of the inner core either by melt coating or solution coating by passing the inner core through a bath, through coating rollers, spraying and/or a die. If it is desired to manufacture the stents of the present invention as a single tubular structure rather than a wound fiber structure, a co-extrusion process would be utilized and the co-extrusion dies would be selected to produce a tube of an appropriate diameter having a hollow inner core, said core having a sufficiently effective thickness, and an outer layer of a sufficiently effective thickness. Also, the fibers useful in manufacturing the stents of the present invention can be manufactured to have a hollow passage through the core if desired.

It is important to recognize that a high-lactide polymer such as 95/5 poly(lactide-co-glycolide) can be used to provide excellent initial mechanical properties and excellent retention of those properties with time. The great disadvantage of utilizing materials such as these (ordinary synthetic absorbable homo- or co-polymers) to form temporary stents is that when devices made from them start to degrade, these devices (mechanically) usually fail by way of a catastrophic failure mechanism.

Cracks that initiate, very rapidly propagate causing the article to "break in two"; hence the term "catastrophic failure". These rapidly propagating cracks start to develop while the material is still substantially very hard. Thus, when the articles start to degrade they initially break into large hard pieces, which then continue to break in much smaller pieces. It should be appreciated that unless constrained, the large pieces can migrate and cause severe anatomical and/or biological consequences prior to degrading into harmless finely divided particles. In particular, in the case of temporary stent made from ordinary synthetic absorbable (homo- or) copolymers, these pieces can obstruct of occlude the lumen that the stents were meant to hold open.

Thus utilizing copolymerization of lactide and glycolide (whether in a random, segmented or block nature-ranging from polyglycolide homopolymer to polylactide homopolymer), a combination of properties, such as suitable initial mechanical properties, suitable excellent retention of those properties with time, and softening failure mechanism, is very difficult if not impossible to achieve.

We have unexpectedly found that the blends described in U.S. Pat. No. 4,889,119 meant to produce absorbable plastic surgical fasteners by injection molding applications, can be utilized to great advantage in producing fibers, which can be made into biodegradable temporary stents. We have further discovered that fiber of the described blend in the form of a hollow fiber construction, and especially in the form of a fiber having an inner core of a second faster degrading material, provides much-preferred embodiments of our present invention.

Although we do not wish to be held to any particular scientific theory or principles, we believe that the blend composition results in a morphology in which the lactide-rich polymers act as a crack arrestor. The cracks that initiate, rather than very rapidly propagating, are arrested. Although these cracks start to develop while the material is still substantially very hard, because the cracks are not allowed to rapidly propagate, the article does not "break in two". In time, the article develops other small cracks; all the while these cracks are prevented from breaking completely through the article by the lactide-rich blend component acting as the "crack arresting" minor phase. This lactide-rich blend component also helps to reinforce the article until there are so many cracks that the article softens and harmlessly fails without producing the large, potentially obstruction or occluding pieces of the prior art.

In another embodiment of the present invention, the polymers and blends that are used to form the composite can be used as a drug delivery matrix. To form this matrix, the polymer would be mixed with a therapeutic agent. The variety of different therapeutic agents that can be used in conjunction with the polymers of the present invention is vast. In general, therapeutic agents which may be administered via the pharmaceutical compositions of the invention include, without limitation: anti-infectives such as antibiotics and anti-viral agents; analgesics and analgesic combinations; anti-inflammatory agents; hormones such as steroids; bone regenerating growth factors; and naturally derived or genetically engineered proteins, polysaccharides, glycoproteins, or lipoproteins.

Matrix formulations may be formulated by mixing one or more therapeutic agents with the polymer. The therapeutic agent may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

The stents 10 of the present invention when made from fiber are manufactured in the following manner using a winding process. A co-extruded fiber is used to wind the stent about a mandrel by heating the fiber and then coiling it around the mandrel. The fiber may be heated prior to winding or subsequent to winding about the mandrel using conventional processes. The assembly of the mandrel and the stent are preferably annealed under constraint and then the mandrel is removed. If desired, the stent may be annealed after removal from the mandrel. The pitch and diameter of the coils are selected to provide the desired size and shape of stent.

The stents of the present invention may be utilized in the following manner in urethral stent placement procedures as illustrated in FIGS. 1, 2, 5, 6, 7 and 8. Initially a stent 10 is placed upon the distal end of an applicator instrument 200. Instrument 200 is seen to have handle 250 having grip 255. At the top 257 of the handle 250 is mounted the shaft retention member 290. Retention member 290 is seen to have longitudinal passageway 292, front 295 and back 296. The mounting tube 240 is seen to have distal end 242 and proximal end 244. Mounting tube 240 is seen to have passage 248. The proximal end 244 of tube 240 is seen to be mounted in passage way 292 such that the inner passageway 248 is in communication with passageway 292. Slidably mounted in passageway 248 is the applicator tube 220. Tube 220 has distal end 222, proximal end 224, and passageway 226. Mounted to the proximal end 224 of tube 220 is the mounting block 300, which is affixed to end 224 by pin 309. Mounted to the bottom of block 300 is rack gear member 330 having gear teeth 335. Contained in handle 250 is the cavity 350 for receiving pinion gear member 270, having teeth 275. Pinion gear member 270 is pivotally mounted in cavity 350 by pivot pins 265. Teeth 275 mesh with and are engaged by teeth 335. Extending out from pinion gear member 270 on the opposite side of pins 265 is the actuation trigger 280. Actuation of trigger 280 will move tube 220 proximally and distally with respect to tube 240. Actuating the trigger 280 will allow the stent 10 to be released from the tubes 220 and 240.

Figure 8:
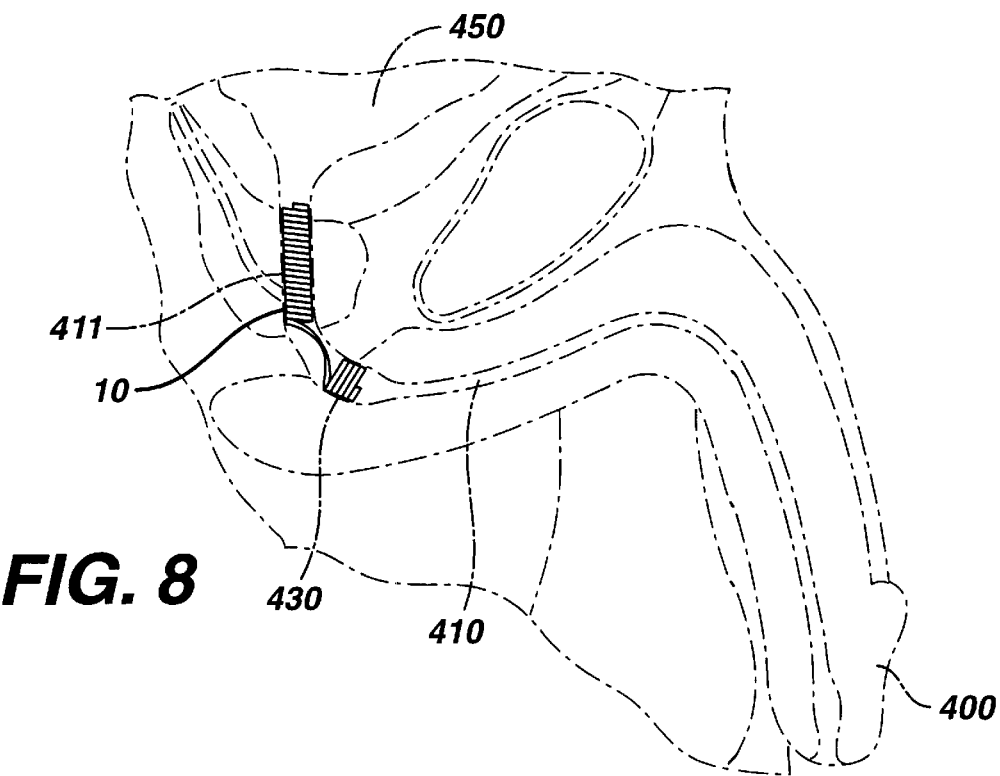
FIG. 8 illustrates the stent of the present invention fully deployed in the urethra and prostate of a patient, providing for a patent lumen.
Figure 9:
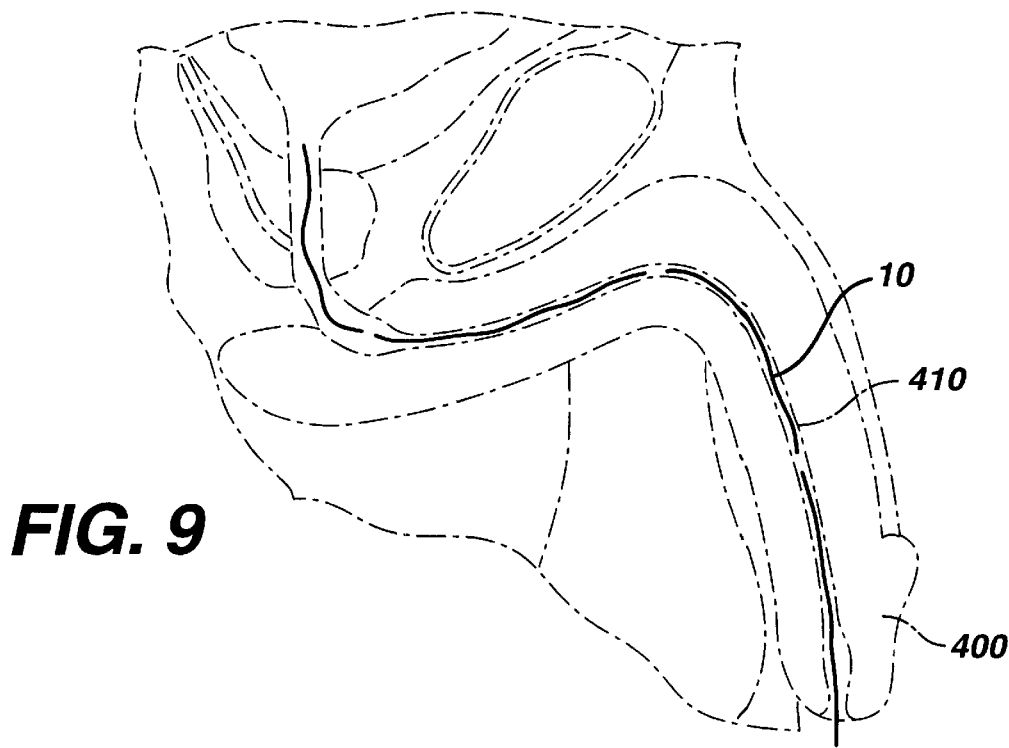
FIG. 9 illustrates a stent of the present invention emplaced in the urethra of a patient after the inner core has broken down and shows the stent being excreted from the body as an elongated soft strand or number of elongated soft strands.

The stent and distal end of the instrument 200 are inserted into the urethra 410 through the meatus 400 of the patient's penis as seen in FIGS. 8 and 9. The distal end of the instrument 200 and the stent 10 are manipulated through the urethra 410 such that the prostatic section of the stent is located within the prostatic urethra 411 and the distal end of the stent is distal to the external sphincter 430, thereby providing an open passage for urine from bladder 450 through the lumen of the urethra. Then, the application instrument 200 is withdrawn from the urethra 410 by engaging trigger 260 and pulling distally on the instrument, thereby completing the procedure and providing for an implanted stent 10 which allows for patency of the urethral lumen 410. As seen in FIG. 9, the stent 10 after having been in place for the appropriate period of time has degraded to a state wherein it is substantially a soft, flexible fragment or filament, or a number of discrete soft, flexible fragment or filaments, and is readily passed from the urethra 410 out of the patient's body with the urine flow. It will be appreciated by those skilled in the art that placement for other types of body lumens could be done in a similar manner, with modification as required by the unique characteristics of the lumen or of the surgical emplacement procedure.

The following examples are illustrative of the principles and practice of the present invention, although not limited thereto.

EXAMPLE 1

A material blend was prepared for use in manufacturing the inner core and outer layer of a fiber useful to wind into a stent of the present invention. The use of this material in fiber formation is described in Example 2.

The outer shell layer was constituted from a blend of 60 wt % of a first random copolymer containing 90 mole % of polymerized glycolide and 10 mole % polymerized lactide and 40 wt % of a second copolymer containing 85 mole % polymerized lactide and 15 mole % polymerized glycolide. The inherent viscosity of the first copolymer containing 90 mole % polymerized glycolide and 10 mole % polymerized lactide, to be henceforth referred to as 90/10 glycolide/lactide copolymer, was 1.4 dL/g as determined in HFIP (hexafluroisopropanol) at 25° C. at a concentration of 0.1 g/dL. The inherent viscosity of the second copolymer containing 85 mole % polymerized lactide and 15 mole % polymerized glycolide, to be henceforth 85/15 lactide/glycolide copolymer, was 2.1 dL/g as determined in chloroform at 25° C. at a concentration of 0.1 g/dL. The two copolymers were mixed into a 60/40 weight ratio before being finally melt blended and pelletized using an 18 mm twin screw extruder with 40:1 L:D, low to medium shear screw configurations and proper venting. The temperature profile was 130, 205, 205, 210, 210, 210 and 205° C. from rear zone to die flange. The die was a single orifice rod die with 2.5 mm diameter and the die temperature was 200° C. The extrudate from the twin screw was quenched in a water bath and pelletized. The inherent viscosity of the first blend containing polymerized glycolide and polymerized lactide was 1.6 dL/g as determined in hexafluroisopropanol at 25° C. at a concentration of 0.1 g/dL.

The inner core layer is constituted from a blend containing 95 wt % of a segmented block copolymer of 75 mole % of a polymerized glycolide and 25 mole % of polymerized caprolactone and 5 wt % of barium sulfate. The inherent viscosity of the segmented block copolymer containing glycolide and caprolactone, to be henceforth to be referred to as 75/25 glycolide/caprolactone, was 1.5 dL/g as determined in hexafluoroisopropanol at 25° C. at a concentration of 0.1 g/dL. The incorporation of barium sulfate allows the fiber to be radio-opaque. The two components were pre-blended at a required 95/5 weight ratio before being finally melt blended and pelletized using an 18 mm twin screw extruder with 40:1 L:D, low to medium shear screw configurations and proper venting. The temperature profile for compounding the core materials was 130, 185, 190, 190, 195, 195 and 195° C., from rear zone to die flange. The die has a single orifice rod die with 2.5 mm diameter and the die temperature was 190° C. The extrudate from the twin screw was quenched in a water bath and pelletized. The inherent viscosity of the second blend containing polymerized glycolide and polymerized caprolactone was 1.5 dL/g as determined in hexafluroisopropanol at 25° C. at a concentration of 0.1 g/dL.

EXAMPLE 2

The fabrication method for coextruded fibers with round cross-sections follows. The material used in the inner core and outer layer shell has been described in Example 1 above. The outer shell layer was made from a blend 60 wt % 90/10 glycolide/lactide copolymer and 40 wt % a 85/15 lactide/glycolide copolymer. The inner layer was made from a blend of 95 wt % of 75/25 glycolide/caprolactone segmented block copolymer and 5 wt. % Barium Sulfate. Also the in vitro tensile testing of the fibers is presented and compared to coextruded fibers that have only the 90/10 glycolide/lactide copolymer.

The fibers were co-extruded using two single screw extruders. Both screws had compression ratios of 3:1 and a 1/D of 25:1. A 1" horizontal extruder was used for outer shell layer and ⅝" vertical extruder was used for the inner core. A concentric two-layer feed-block was used to feed the two material stream into a single orifice die from which the extrudate is fed to a water trough for cooling. An air jet was used to remove the excess surface moisture and an air cutter was used to cut fiber into desired length of approximately 4 feet. A laser-micrometer was used to measure the fiber diameter (major and minor) on-line and a microscope was used to ascertain the wall thickness, of the inner and outer layers.

The temperature profile of the material in the outer shell was 185, 210, 222, 215, and 215° C. from rear barrel zone to die flange. The blend in the outer shell was 60 wt % of 90/10 glycolide/lactide copolymer and 40 wt % of 85/15 lactide/glycolide copolymer. The temperature profile of the inner core material was 215, 224, 224 and 230° C. from rear barrel zone to die flange. The material in the inner core was a blend of 95 wt % 75/25 glycolide/caprolactone segmented block copolymer and 5 wt. % $BaSO_4$. A single-hole die of circular cross-section at a temperature of 213° C. was used.

Figure 16:
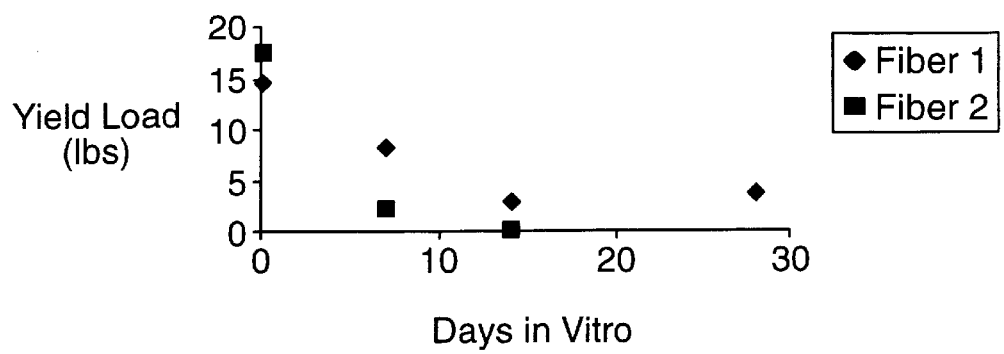
FIG. 16 is a graph of Yield Loads vs Days In Vitro of coextruded fibers with an overall diameter of 1 mm (40 mils) and an outer shell thickness of 0.2 mm (8 mils). Fiber 1 has an outer layer composed from a blend containing 60 weight percent of a copolymer of 90 mole % glycolide and 10 mole % of lactide and 40 weight percent of a second copolymer of 15 mole % glycolide and 85 mole % of lactide. The inner layer of Fiber 1 is composed from a blend of 95 weight percent of a copolymer of glycolide and caprolactone and 5 weight percent of barium sulfate. Fiber 2 has an outer layer composed from a copolymer of 90 mole % glycolide and 10 mole % of lactide. Inner layer of Fiber 2 is composed from a blend of weight percent of a copolymer of glycolide and caprolactone and 5 weight percent of barium sulfate.
Figure 17:
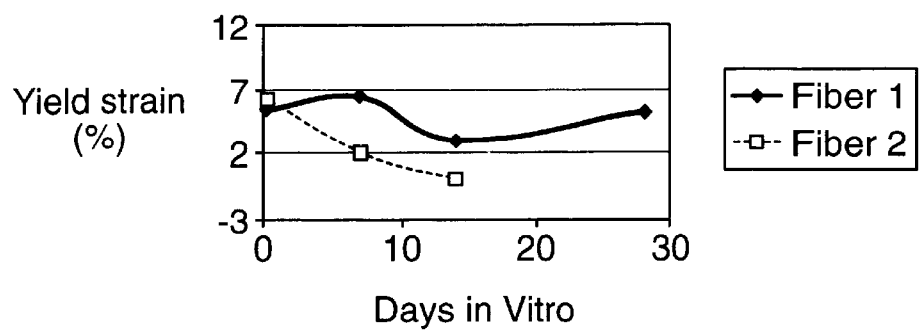
FIG. 17 is a graph of Yield Strain vs Days In Vitro of coextruded fibers with an overall diameter of 1 mm (40 mils) and an outer shell thickness of 0.2 mm (8 mils). Fiber 1 has an outer layer composed from a blend containing 60 wt % of a copolymer of 90 mole % glycolide and 10 mole % of lactide and 40 wt % of a second copolymer of 15 mole % glycolide and 85 mole % of lactide. Inner layer of Fiber 1 is composed from a blend of 95 wt of a copolymer of glycolide and caprolactone and 5 wt % of barium sulfate. Fiber 2 has an outer layer composed from a copolymer of 90 mole % glycolide and 10 mole % of lactide. Inner layer of Fiber 2 is composed from a blend of 95 wt of a copolymer of glycolide and caprolactone and 5 wt % of barium sulfate.

The in vitro yield load and yield strain of the coextruded round fiber, made by the above mentioned method, are compared in FIGS. 16 and 17 to that of a coextruded round fiber having a different material composition in the outer shell. Both fibers are 1 mm (40 mils) diameter with an outer wall thickness of 0.2 mm (8 mils). The inner core composition of both fibers is the same; i.e. was a blend of 95 weight percent 75/25 glycolide/caprolactone segmented block copolymer and 5 weight percent $BaSO_4$. The outer shell for the first round fiber was made from a blend containing 60 weight percent of a copolymer of 90/10 glycolide/lactide copolymer and 40 weight percent of 85/15 lactide/glycolide copolymer. However, the outer shell layer of the second round fibers was made from 90/10 glycolide/lactide copolymer. Both fibers were annealed at 75° C. for 6 hours.

The tensile tests on the fibers were conducted using an Instron 4500 and the fiber samples were pulled at a speed of 30.5 mm/minute and the sample length was 25.4 mm. The load at yield and the strain at yield were measured. For in vitro testing, the samples kept in a phosphate buffered solution bath with a pH of 7.27 at a temperature of 37 C. Samples were removed from the bath at stated intervals and tested for yield load and yield strain.

The complete loss of yield load within 10 days of the second coextruded round fiber (which did not have a blended material in the outer shell) demonstrates the significance of adding a lactide-rich copolymer, i.e. 85/15 lactide/glycolide copolymer to the glycolide-rich copolymer, i.e. 90/10 glycolide/lactide copolymer, in the first round fiber. The yield strain, for the first fibers with the blended material in the outer shell, drops but recovers owing to the presence of the lactide-rich component. The lactide-rich component is likely to provide toughness to the shell material of the first round fiber at longer in vitro exposure compared to the shell materials in the second round coextruded fiber that only contains glycolide-rich copolymer.

EXAMPLE 3

A process used to convert fibers having an oval or elliptical cross-section into stents is described in this example. A stent with single helix structure was formed from a single oval fiber. Coextruded fibers containing materials made in Example 1 were considered for the shell and core of the oval fiber.

The process to make oval coextruded fibers is described first. The material used in the outer core and inner shell has been described in Example 1. The outer shell layer was made from a blend 60 wt % of 90/10 glycolide/lactide copolymer and 40 wt % of 85/15 lactide/glycolide copolymer. The inner layer was made from a blend of 95 wt % of 75/25 glycolide/caprolactone segmented block copolymer and 5 wt.% barium sulfate.

The oval fibers were coextruded using two single screw extruders. Both screws had compression ratios of 3:1 and a L/D of 25:1. A 1" horizontal extruder was used for outer shell layer and ⅝" vertical extruder was used for the inner core. A concentric two-layer feed-block feeds the two material stream into a single orifice die from which the extrudate is fed to a water trough for cooling. An air jet was used to remove the excess surface moisture and an air cutter is used to cut fiber into desired length of approximately 4 feet. A laser-micrometer was used to measure the fiber diameter (major and minor) on-line and a microscope was used to ascertain the wall thickness, of the inner and outer layers.

The temperature profile of the material in the outer shell was 185, 210, 222, 215, and 215° C. from rear barrel zone to die flange. The blend in the outer shell was 60 wt % of 90/10 glycolide/lactide copolymer and 40 wt % of 85/15 lactide/glycolide copolymer. The temperature profile of the inner core material was 215, 224, 224and 230° C. from rear barrel zone to die flange. The material in the inner core was a blend of 95 weight percent of 75/25 glycolide/caprolactone segmented block copolymer and 5 weight percent barium sulfate. A single-hole die of oval cross-section at 213° C. was used.

The dimension of the coextruded oval fiber was 1 mm (40 mils) minor diameter and a 2 mm (80 mils) major diameter with a 0.2 mm (8 mil) outer wall thickness.

Figure 18:
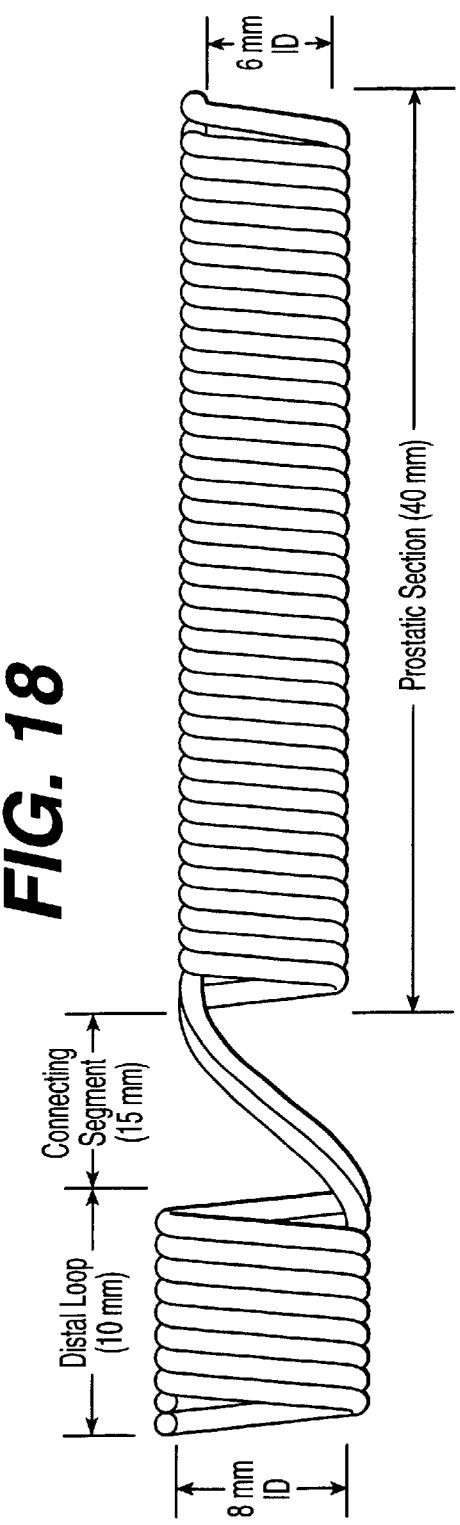
FIG. 18 is a side view of a schematic of a stent with critical dimensions referred to in Example 3.
Figure 19:
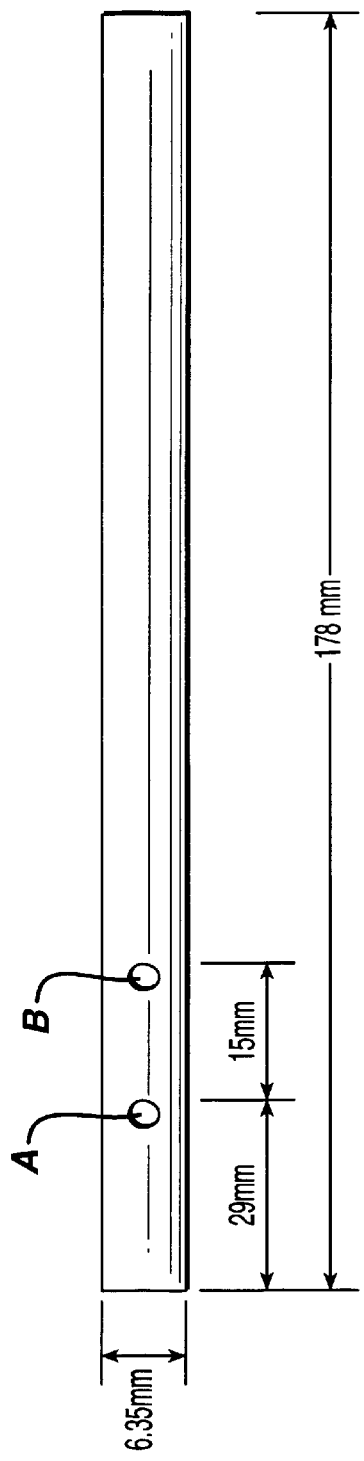
FIG. 19 is a schematic of a mandrel used to manufacture stents in Example 3.

The fibers were wound on mandrels at elevated temperatures. The mandrels were made from reinforced plastics. The shape and dimensions of the mandrel is shown in FIG. 18. The winding temperature was 70 C.

The oval fiber major diameter of 80 mils and minor diameter of 40 mils) measuring 4 feet long was held and taped against mandrel at about 60 mm from hole B. Two metal posts ($\phi 2 \times 15$ mm length) are inserted into the holes A and B. The mandrel and fiber were immersed in a constant temperature water bath at 70° C. and held there for one minute. By using appropriately positioned clamps, it was ensured the entire fiber was under tension while being immersed and that the fiber was guided into closely packed coils. The winder rotated the mandrel between 20–30 RPM to form the prostatic section.

The coiling process started from the taped point and the prostatic portion was complete when the coils reach the post at point B. The fiber was then guided at an angle of 180° or more over the post B towards second post C to form the connector. The fiber was then guided at a rotation of 180° or more over the post B towards second post A to form the connector. The fiber was then guided back to a position perpendicular to the mandrel before being coiled to form the distal loop section of the stent.

The entire assembly, i.e. the coiled stent and the mandrel was removed from the bath and the unused fiber cut off and discarded. The assembly of mandrel and stent was dried under vacuum for at least 48 hours prior to annealing.

EXAMPLE 4

The stents were annealed after they were wound. Prior to annealing, the posts or pins were removed from the mandrel. The entire assembly, of stent wound on mandrel, was then hung in an inert gas (nitrogen) annealing oven, the oven purged and the stent annealed at 75° C. for 6 hours. The stents are removed from the mandrel and stored in nitrogen box.

EXAMPLE 5

In vitro testing on stents made in Example 4 was conducted to determine how the stents would withstand radial stresses. The testing provided the in vitro (tested in phosphate buffered solution with pH of 7.3 and temperature of 37° C.) compressive crush resistance test results for single helix stents made from oval fibers.

The prostatic coil section of a stent was cut from the whole stent and was held between a fixed bottom plate and a movable upper plate in an Instron 1122 tensile testing machine. The top plate was moved at a speed of 2.5 mm per minute. The radial compressive stiffness and the maximum compressive load that the coils withstood during the deformation rate of 2.5 mm per minute, are shown in the table.

TABLE

In Vitro Radial Compressive Test for the Prostatic Coils

Oval fiber with 0.2 mm outer wall

| Days | Max. Load (lbs) | Radial Stiffness Resistance (lbs/inch) |
| --- | --- | --- |
| 0 | 40 | 2710 |
| 7 | 37 | 1505 |
| 10 | 27 | 1490 |
| 14 | 20 | 1154 |

Over the 14 day period, both the maximum load and stiffness decreased with increased in vitro exposure. Coils made from oval coextruded fibers with 0.2 mm (8 mil) wall and having the composition described in Example 3 lost their properties gradually. However, a stent made from round coextruded fibers having a 90/10 glycolide/lactide copolymer in the outer shell and a blend of 95 wt % 75/25 glycolide/caprolactone segmented block copolymer and 5 wt. % barium sulfate in the inner core collapsed with 10 days of in vitro exposure.

Compared to a typical removable catheter such as a Foley catheter that is used to keep the uretheral lumen open, maximum load and stiffness of stents made from oval fiber is higher than those of Foley catheters even after 14 days of in vitro exposure. This indicates that stents, made from coextruded fibers having the particular composition described in Example 4, have sufficient adequate mechanical response necessary to keep the urethra patent and functional at least 14 days.

EXAMPLE 6

The previous example demonstrated the efficacy of stents made from coextruded fibers after prolonged in vitro exposure. With further exposure to in vitro medium, the inner core and the outer shell of fibers, from which the stent is made, degrades at different rates. The resultant morphology of the stent is obtained by observing the cross-section of the fibers under a scanning electron microscope.

Figure 20A:
FIGS. 20A–C illustrates electron microscope photographs discussed in Example 6.
Figure 20B:
Figure 20C:

The scanning electron micrographs shown in FIGS. 20A–C show the cross-section of oval fibers from stents that have undergone in vitro exposure at 14, 28 and 42 days. It is apparent that the core was degrading faster than the shell. The faster degrading core posses no mechanical integrity and has been slowly removed. The slower degrading shell retained fibrillar morphological structure even at longer time periods. The effect of the differing degradation profiles and the physical state of the degraded polymers reduce the stent cross-section from a solid to a soft structure that increasingly appears to be hollow. The fibrillar structure will soften over time instead of breaking down into large sharp fragments that can cause the removal and/or passage of the degraded stent to be clinically eventful. In a flow environment, the progressively degrading stent can readily pass through the body lumen without causing obstruction, pain or discomfort.

EXAMPLE 7

A male patient is appropriately anesthetized and undergoes a prostrate thermal ablation procedure using conventional laser treatment devices. After successful completion of the surgical procedure, a stent 5 of the present invention is inserted into the patient's urethra and bladder in the following manner using an applicator 200: The surgeon trims the stent to size. The stent is placed at the end of the applicator. A conventional cystoscope is inserted into the lumen of the applicator. The stent and applicator are lubricated with a water soluble medical grade lubricant. A fluid reservoir is attached to the applicator as in any standard cystoscopy procedure. The stent is placed in the prostatic urethra under direct visualization using a scope. Once positioned correctly, the applicator is removed, leaving behind the stent in the prostatic urethra. In approximately 28 days after implantation, the stent breaks down into fibrillar structure that softens further and is passed from the urinary tract in several soft pieces through normal urine voiding.

The stents of the present invention provide many advantages over the stents of the prior art. The advantages include: rigidity (lumen patency) for a prescribed time; a degradation softening mechanism, whereby the stent softens into a readily passable fragment or fragments; biocompatibility; means to prevent migration; means to non-invasively monitor the stent and its position by X-ray. etc.

Although this invention has been shown and described with respect to detailed embodiments thereof, it will be understood by those skilled in the art that various changes in form and detail may be made without departing from the spirit and scope of the claimed invention.

We claim:

1. A stent, comprising:

a tubular structure having a longitudinal passage, said structure comprising:

an inner core having an exterior surface comprising a biodegradable polymer formed from monomers selected from the group consisting of lactide, glycolide, para-dioxanone, trimethylene carbonate, caprolactone, and combinations thereof, said polymer having a first degradation rate;

an outer section covering the exterior surface of the inner core, the outer section comprising a blend of a first biodegradable polymer component and a second biodegradable polymer component, said first polymer component comprising a first biodegradable polymer, wherein said first biodegradable polymer comprises a lactide/glycolide copolymer having at least about 80 mole percent of polymerized glycolide, said second polymer component comprising a second biodegradable polymer, wherein said second biodegradable polymer comprises a lactide-rich copolymer comprising at least about 50 mole percent of polymerized lactide, said outer layer having a second degradation rate, wherein the blend comprises at least about 50 weight percent of the first component and at least about 5 weight percent of the second component, wherein said second degradation rate of said outer layer is slower than said first degradation rate of the inner core.

2. The stent of claim 1, wherein the outer structure comprises a lattice having openings therein.

* * * * *